(12) United States Patent
Sarac

(10) Patent No.: US 11,890,181 B2
(45) Date of Patent: *Feb. 6, 2024

(54) PERCUTANEOUS ENDOVASCULAR APPARATUS FOR REPAIR OF ANEURYSMS AND ARTERIAL BLOCKAGES

(75) Inventor: Timur P. Sarac, Chagrin Falls, OH (US)

(73) Assignee: TMT Systems, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/484,331

(22) Filed: Jul. 10, 2006

(65) Prior Publication Data
US 2007/0168017 A1 Jul. 19, 2007

Related U.S. Application Data

(63) Continuation-in-part of application No. 10/624,864, filed on Jul. 22, 2003, now Pat. No. 7,101,393.
(Continued)

(51) Int. Cl.
*A61F 2/07* (2013.01)
*A61F 2/89* (2013.01)
(Continued)

(52) U.S. Cl.
CPC ............... *A61F 2/07* (2013.01); *A61F 2/848* (2013.01); *A61F 2/89* (2013.01);
(Continued)

(58) Field of Classification Search
CPC .... A61F 2/07; A61F 2/848; A61F 2/89; A61F 2002/065; A61F 2002/826;
(Continued)

(56) References Cited

U.S. PATENT DOCUMENTS 3,174,851 A 3/1965 Buchler et al.
3,351,462 A 11/1967 Arentzen et al.
(Continued)

FOREIGN PATENT DOCUMENTS

EP 0 947 179 A2 10/1999
EP 1 138 279 A2 10/2001
(Continued)

OTHER PUBLICATIONS

Office Action received in U.S. Appl. No. 10/624,864, dated Oct. 5, 2004.
(Continued)

*Primary Examiner* — Christopher D. Prone
(74) *Attorney, Agent, or Firm* — McBee, Moore & Vanik IP, LLC

(57) ABSTRACT

An endovascular apparatus is provided for treating the effects of vascular disease including aneurysms and arterial blockages using a percutaneous, minimally invasive technique. In one embodiment the endovascular apparatus includes a tubular sleeve having a cranial end, a first caudal branch, and a second caudal branch such that the tubular sleeve is shaped like an upside down "Y." The apparatus further includes at least one expandable attachment device attached to the tubular sleeve for securing the endovascular apparatus to an interior wall of a vessel. The at least one expandable attachment device includes a plurality of telescoping segments similar to the telescoping segments of a presentation pointer. Accordingly, during percutaneous insertion of the endovascular apparatus into a patient the attachment device can be collapsed into a small profile. Once positioned at the site of the aneurysm the telescoping attachment device can be expanded to hold the endovascular apparatus in place adjacent the inner lumen wall.

12 Claims, 10 Drawing Sheets

Related U.S. Application Data

(60) Provisional application No. 60/397,745, filed on Jul. 22, 2002.

(51) Int. Cl.
*A61F 2/848* (2013.01)
*A61F 2/06* (2013.01)
*A61F 2/82* (2013.01)

(52) U.S. Cl.
CPC ... *A61F 2002/065* (2013.01); *A61F 2002/075* (2013.01); *A61F 2002/826* (2013.01); *A61F 2220/005* (2013.01); *A61F 2220/0016* (2013.01); *A61F 2220/0075* (2013.01); *A61F 2230/005* (2013.01); *A61F 2230/0017* (2013.01); *A61F 2230/0054* (2013.01); *A61F 2250/001* (2013.01); *A61F 2250/0007* (2013.01)

(58) Field of Classification Search
CPC .......... A61F 2002/075; A61F 2230/005; A61F 2230/0054; A61F 2250/001; A61F 2220/0016; A61F 2220/005; A61F 2220/0075; A61F 2230/0017; A61F 2230/0056; A61F 2002/8483; A61F 2002/8486
USPC ................................ 623/1.15, 1.3, 1.35, 1.36
See application file for complete search history.

(56) References Cited

U.S. PATENT DOCUMENTS

| | | | |
|---|---|---|---|
| 3,753,700 A | 8/1973 | Harrison et al. | |
| 4,505,767 A | 3/1985 | Quin | |
| 4,665,906 A | 5/1987 | Jervis | |
| 5,064,435 A * | 11/1991 | Porter | 623/23.7 |
| 5,104,399 A | 4/1992 | Lazarus | |
| 5,123,917 A | 6/1992 | Lee | |
| 5,226,913 A | 7/1993 | Pinchuk | |
| 5,282,824 A | 2/1994 | Gianturco | |
| 5,316,023 A | 5/1994 | Palmaz et al. | |
| 5,360,443 A | 11/1994 | Barone et al. | |
| 5,387,235 A * | 2/1995 | Chuter | 623/1.11 |
| 5,397,345 A | 3/1995 | Lazarus | |
| 5,456,713 A | 10/1995 | Chuter | |
| 5,489,295 A * | 2/1996 | Piplani et al. | 623/1.35 |
| 5,562,726 A | 10/1996 | Chuter | |
| 5,571,173 A | 11/1996 | Parodi | |
| 5,575,817 A | 11/1996 | Martin | |
| 5,609,627 A * | 3/1997 | Goicoechea | A61F 2/07 128/898 |
| 5,628,783 A * | 5/1997 | Quiachon | A61F 2/07 606/194 |
| 5,632,772 A * | 5/1997 | Alcime et al. | 623/1.35 |
| 5,676,696 A * | 10/1997 | Marcade | 623/1.35 |
| 5,681,346 A | 10/1997 | Orth et al. | |
| 5,693,088 A * | 12/1997 | Lazarus | 623/1.35 |
| 5,713,917 A | 2/1998 | Leonhardt et al. | |
| 5,755,777 A | 5/1998 | Chuter | |
| 5,755,778 A | 5/1998 | Kleshinski | |
| 5,797,951 A | 8/1998 | Mueller | |
| 5,800,526 A | 9/1998 | Anderson et al. | |
| 5,824,037 A | 10/1998 | Fogarty et al. | |
| 5,824,041 A | 10/1998 | Lenker et al. | |
| 5,824,044 A * | 10/1998 | Quiachon et al. | 623/1.23 |
| 5,843,164 A | 12/1998 | Frantzen et al. | |
| 5,843,167 A | 12/1998 | Dwyer et al. | |
| 5,851,228 A * | 12/1998 | Pinheiro | 623/1.13 |
| 5,855,601 A | 1/1999 | Bessler et al. | |
| 5,871,536 A | 2/1999 | Lazarus | |
| 5,919,225 A | 7/1999 | Lau et al. | |
| 5,961,545 A * | 10/1999 | Lentz et al. | 623/1.39 |
| 5,984,955 A | 11/1999 | Wisselink | |
| 6,010,530 A | 1/2000 | Goicoechea | |
| 6,027,525 A | 2/2000 | Suh et al. | |
| 6,042,605 A | 3/2000 | Martin et al. | |
| 6,066,168 A | 5/2000 | Lau et al. | |
| 6,071,308 A | 6/2000 | Ballou et al. | |
| 6,083,258 A * | 7/2000 | Yadav | 623/1.15 |
| 6,086,611 A | 7/2000 | Duffy et al. | |
| 6,099,558 A * | 8/2000 | White et al. | 623/1.16 |
| 6,132,457 A | 10/2000 | Chobotov | |
| 6,156,064 A | 12/2000 | Chouinard | |
| 6,165,214 A * | 12/2000 | Lazarus | 623/1.35 |
| 6,221,102 B1 * | 4/2001 | Baker | A61B 17/11 623/1.13 |
| 6,264,684 B1 | 7/2001 | Banas et al. | |
| 6,273,909 B1 | 8/2001 | Kugler et al. | |
| 6,287,315 B1 | 9/2001 | Wijeratne et al. | |
| 6,290,731 B1 | 9/2001 | Solovay et al. | |
| 6,306,141 B1 | 10/2001 | Jervis | |
| 6,309,343 B1 | 10/2001 | Lentz et al. | |
| 6,312,460 B2 * | 11/2001 | Drasler et al. | 623/1.15 |
| 6,319,277 B1 | 11/2001 | Rudnick et al. | |
| 6,331,188 B1 | 12/2001 | Lau et al. | |
| 6,334,867 B1 | 1/2002 | Anson | |
| 6,334,869 B1 | 1/2002 | Leonhardt et al. | |
| 6,361,637 B2 | 3/2002 | Martin et al. | |
| 6,368,345 B1 | 4/2002 | Dehdashtian et al. | |
| 6,409,756 B1 * | 6/2002 | Murphy | A61F 2/07 623/1.16 |
| 6,423,090 B1 | 7/2002 | Hancock | |
| 6,482,227 B1 | 11/2002 | Solovay | |
| 6,517,570 B1 | 2/2003 | Lau et al. | |
| 6,520,986 B2 | 2/2003 | Martin et al. | |
| 6,524,335 B1 | 2/2003 | Hartley et al. | |
| 6,551,350 B1 * | 4/2003 | Thornton et al. | 623/1.13 |
| 6,565,596 B1 | 5/2003 | White et al. | |
| 6,579,307 B2 | 6/2003 | Sarac | |
| 6,652,580 B1 | 11/2003 | Chuter et al. | |
| 6,695,875 B2 | 2/2004 | Stelter et al. | |
| 6,860,901 B1 | 3/2005 | Baker et al. | |
| 6,878,161 B2 | 4/2005 | Lenker | |
| 6,929,661 B2 | 8/2005 | Bolduc et al. | |
| 6,945,992 B2 | 9/2005 | Goodson, IV et al. | |
| 6,951,571 B1 * | 10/2005 | Srivastava | 623/1.24 |
| 7,101,393 B2 * | 9/2006 | Sarac | 623/1.36 |
| 7,264,632 B2 | 9/2007 | Wright et al. | |
| 7,331,992 B2 | 2/2008 | Randall et al. | |
| 7,615,072 B2 | 11/2009 | Rust et al. | |
| 7,722,622 B2 | 5/2010 | Steinke et al. | |
| 7,722,662 B2 * | 5/2010 | Steinke et al. | 623/1.16 |
| 8,172,895 B2 * | 5/2012 | Anderson | A61F 2/07 623/1.11 |
| 8,206,427 B1 | 6/2012 | Ryan et al. | |
| 8,323,328 B2 | 12/2012 | Martin et al. | |
| 8,623,065 B2 | 1/2014 | Lau et al. | |
| 8,663,307 B2 | 3/2014 | Arbefeuille | |
| 8,702,787 B2 | 4/2014 | Arbefeuille | |
| 9,717,585 B2 | 8/2017 | Sarac | |
| 9,956,070 B2 | 5/2018 | Sarac | |
| 2001/0037142 A1 | 11/2001 | Stelter et al. | |
| 2001/0049550 A1 | 12/2001 | Martin et al. | |
| 2001/0053930 A1 | 12/2001 | Kugler et al. | |
| 2002/0002397 A1 | 1/2002 | Martin et al. | |
| 2002/0138131 A1 | 9/2002 | Jacobs et al. | |
| 2002/0156521 A1 * | 10/2002 | Ryan et al. | 623/1.13 |
| 2002/0156523 A1 | 10/2002 | Lau et al. | |
| 2002/0177890 A1 | 11/2002 | Lenker | |
| 2003/0088305 A1 | 5/2003 | Van Schie et al. | |
| 2003/0120338 A1 | 6/2003 | Chobotov et al. | |
| 2003/0130721 A1 | 7/2003 | Martin et al. | |
| 2003/0199967 A1 * | 10/2003 | Hartley | A61F 2/07 623/1.13 |
| 2004/0082989 A1 | 4/2004 | Cook et al. | |
| 2004/0093063 A1 | 5/2004 | Wright et al. | |
| 2004/0260383 A1 | 12/2004 | Stelter et al. | |
| 2005/0021132 A1 | 1/2005 | Bolduc et al. | |
| 2005/0113933 A1 | 5/2005 | Carter et al. | |
| 2005/0222669 A1 | 10/2005 | Purdy | |
| 2006/0178733 A1 * | 8/2006 | Pinchuk | A61F 2/07 623/1.35 |

(56) References Cited

U.S. PATENT DOCUMENTS

| | | |
|---|---|---|
| 2007/0055345 A1 | 3/2007 | Arbefeuille |
| 2007/0055347 A1 | 3/2007 | Arbefeuille |
| 2007/0142894 A1 | 6/2007 | Moore et al. |
| 2007/0168017 A1* | 7/2007 | Sarac .............. 623/1.16 |
| 2008/0011441 A1 | 1/2008 | Oswald et al. |
| 2010/0016948 A1* | 1/2010 | Chobotov .............. 623/1.13 |
| 2011/0178591 A1 | 7/2011 | Sarac |
| 2016/0058547 A1 | 3/2016 | Sarac |
| 2016/0058587 A1 | 3/2016 | Sarac |
| 2017/0035547 A1 | 2/2017 | Sarac |

FOREIGN PATENT DOCUMENTS

| | | | |
|---|---|---|---|
| EP | 1534182 A1 | 6/2005 | |
| WO | 9508966 A1 | 4/1995 | |
| WO | 9521592 A1 | 8/1995 | |
| WO | WO 97/12562 A1 * | 4/1997 | .............. A61F 2/04 |
| WO | 1998053761 A1 | 12/1998 | |
| WO | 1999029262 A1 | 6/1999 | |
| WO | 2001039696 A1 | 6/2001 | |
| WO | WO 2004/008996 A1 | 1/2004 | |

OTHER PUBLICATIONS

Amendment and Interview Summary submitted in U.S. Appl. No. 10/624,864, dated Dec. 22, 2004.
Restriction Requirement received in U.S. Appl. No. 10/624,864, dated Mar. 24, 2005.
Amendment and Response to Restriction Requirement submitted in U.S. Appl. No. 10/624,864, dated Apr. 21, 2005.
Interview Summary received in U.S. Appl. No. 10/624,864, dated May 5, 2005.
Office Action received in U.S. Appl. No. 10/624,864, dated Sep. 9, 2005.
Amendments, Response to Office Action and Interview Summary submitted in U.S. Appl. No. 10/624,864, dated Sep. 22, 2005.
Office Action received in U.S. Appl. No. 10/624,864, dated Nov. 17, 2005.
Amendment and Response to Final Office Action submitted in U.S. Appl. No. 10/624,864, dated Jan. 9, 2006.
Dacron status printout from the USPTO Trademark Electronic Search System, printed from web on Jan. 5, 2009.
Dacron definition, Free Online Medical Dictionary, printed from web on Jan. 5, 2009.
International Search Report for International Application No. PCT/US03/22726, dated Dec. 2, 2003.
J. C.Parodi, "Endovascular Repair of Abdominal Aortic Aneurysms," Advances in Vascular Surgery, (1993), vol. 1, 85.
Charles T. Dotter, et al., "Transluminal Expandable Nitinol Coil Stent Grafting Report", Radiology, (1983), vol. 147, 259-260. [Abstract Only].
Andrew Cragg, et al., "Nonsurgical Placement of Arterial Endoprostheses: A New Technique Using Nitinol Wire," Radiology, (1983), vol. 147, 261-263. [Abstract Only].
Frank J. Criado, et al., "Endovascular Grafting of Abdominal Aortic Aneurysms (AAA): Historical Development and Evolving Technologies," The Journal of Invasive Cardiology, (1999), vol. 11 , No. 9, 577-581. [Bibliographic Info].
Frank J. Criado, et al., "Abdominal Aortic Aneuysm: Overview of Stent-Graft Devices," Journal of the American College of Surgeons, (2002), vol. 194, No. 1, S88-S97. [Abstract Only].
H. M. Lazarus, "Endovascular Grafting for the Treatment of Abdominal Aortic Aneurysms," Surgical Clinics of North America, (1992), vol. 74, No. 4, 959-968. [Abstract Only].
Juan C. Parodi, et al., "Endoluminal Aortic Aneurysm Repair Using a Balloon-Expandable Stent-Graft Device: A Progress Report," Annals Vascular Surgery, (1994). 523-529. [Abstract Only].
Matthew M. Thompson et al., "Aortomonoiliac Endovascular Grafting: Difficult Solutions to Difficult Aneurysms," Journal of Endovascular Surgery, (1997), vol. 4.2, 174-181. [Abstract and Summary Only].

J. Adam Van der Vliet, et al., "Abdominal aortic aneurysm," The Lancet, (1997), vol. 349.9055, 863-866.
S.W. Yusuf, et al., "Transfemoral endoluminal repair of abdominal aneurysm with bifurcated graft," The Lancet, (1994), vol. 344.8923, 650-651. [Abstract Only].
J.C. Parodi, et al., "Transfemoral Intraluminal Graft Implantation for Abdominal Aortic Aneurysms," Annals Vascular Surgery, (1991), vol. 5, No. 6, 491-499.
J. C. Parodi, "Endovascular Repair of Abdominal Aortic Aneurysms," Haimovici's Vascular Surgery: Fifth Edition, (2004), 736-743.
David Milrich, et al., "Percutaneously Placed Endovascular Grafts for Aortic Aneurysms: Feasibility Study," Radiology, (1989), vol. 170, 1033-1037. [Abstract Only].
Frank J. Criado, et al., Early Experience with the Talent Stent-Graft System for Endoluminal Repair of Abdominal Aortic Aneurysms, Texas Heart Institute Journal, (2000), vol. 27, No. 2 : 128.
Alexander Balko, et al., "Transfemoral Placement of Intraluminal Polyurethane Prosthesis for Abdominal Aortic Aneurysm," Journal of Surgical Research, (1986), vol. 40, No. 4: 305-309. [Abstract].
Cherrie Z. Abraham, et al., "Abdominal 2002 aortic aneurysm repair with the Zenith stent graft: Short to midterm results," Journal of Vascular Surgery, (2002), vol. 36, No. 2: 217-225.
Brent T. Allen, et al., "Endovascular Stent Grafts for Aneurysmal and Occlusive Vascular Disease," The American Journal of Surgery, (1998), vol. 176, No. 6 : 574-580.
Ruth L. Bush, et al., "Early experience with the bifurcated Excluder endoprosthesis for treatment of the abdominal aortic aneurysm," Journal of Vascular Surgery, (2001), vol. 34, No. 3, 497-502.
Jeffrey P. Carpenter and Endologix Investigators, "Multicenter trial of 2002 the PowerLink bifurcated system for endovascular aortic aneurysm repair," Journal of Vascular Surgery, (2002), vol. 36, No. 6, 1129-1137.
Timothy A.M. Chuter, et al., "Clinical experience with a bifurcated endovascular graft for abdominal aortic aneurysm repair," Journal of Vascular Surgery, (1996), vol. 24, No. 4, 655-66.
W. Darrin Clouse, et al., "Durability of aortouniiliac endografting with femorofemoral crossover: 4-year experience in the EVT/Guidant trials," Journal of Vascular Surgery, (2003), vol. 37, No. 6: 1142-1149.
Frank J. Criado, et al., "Update on the Talent aortic stentgraft: A preliminary report from United States phase I and II trials," Journal of Vascular Surgery, (2001), vol. 33, No. 2, 146-149.
Roy K. Greenberg, et al., "An update of the 2001 Zenith endovascular graft for abdominal aortic aneurysms: Initial implantation and mid-term follow up data," Journal of Vascular Surgery, (2001), vol. 33, No. 2 157-164.
Marcus H. Howell et al., "Results of Endovascular Abdominal Aortic Aneurysm Exclusion With the AneuRx Stent-Graft," Journal of the American College of Cardiology, (2001), vol. 38, No. 4, 1040-1046.
Marcus Howell, et al., "Percutaneous 2002 Repair of Abdominal Aortic Aneurysms Using the AneuRx Stent Graft and the Percutaneous Vascular Surgery Device," Catheterization and Cardiovascular Interventions, (2002), vol. 55, No. 3: 281-287. [Abstract Only].
Michel S. Makaroun, "The Ancure 2001 endografting system: An update," Journal of Vascular Surgery, (2001), vol. 33, No. 2, 129-134.
Jon S. Matsumura, et al., "Update on the 2001 bifurcated Excluder endoprosthesis: Phase I results," Journal of Vascular Surgery, (2001), vol. 33, No. 2, 150-153.
Jon S. Matsumura, et al., "A multicenter 2003 controlled clinical trial of open versus endovascular treatment of abdominal aortic aneurysm," Journal of Vascular Surgery, (2003), vol. 37, No. 2, 262-271.
Juan Carlos Parodi, "Endovascular repair of abdominal aortic aneurysms and other arterial lesions," Journal of Vascular Surgery, (1995), vol. 21, No. 4, 549-557.
T. Pfammatter, et al., "Repair of abdominal 2003 aortic aneurysms with the Excluder bifurcated stentgraft," Journal of Cardiovascular Surgery, (2003), vol. 44, 549-552.

(56) References Cited

OTHER PUBLICATIONS

Venkatesh G. Ramaiah, et al., "The 2002 AneuRx Stent-Graft Since FDA Approval: Single-Center Experience of 230 Cases," Journal of EndovascularTherapy, (2002), vol. 9, No. 4: 464-469.

T. Resch, et al., "The Impact of Stent Design on Proximal Stent-graft Fixation in the Abdominal Aorta: an Experimental Study," European Journal of Vascular and Endovascular Surgery, (2000), vol. 20, No. 2, 190-195.

M. H. Seelig, et al., "Endovascular Repair of Abdominal Aortic Aneurysms: Where Do We Stand?," Mayo Clinic Proceedings, (1999), vol. 74, No. 10. [Abstract Only].

Charles P. Semba, et al., "Abdominal Aortic Aneurysm Repair With the W.L. Gore Excluder Endovascular Stent-Graft: Technique and Potential Pitfalls," Techniques in Vascular and Interventional Radiology, (1999), vol. 2, 127.

Manfred Tillich, et al., "Helical CT Angiography of Stent-Grafts in Abdominal Aortic Aneurysms: Morphologic Changes and Complications," Radiographics, (1999), vol. 19, No. 6, 1573-1583.

Rodney A. White, "Clinical and design update on the development and testing of a one-piece, bifurcated, polytetrafluoroethylene endovascular graft for abdominal aortic aneurysm exclusion: The Endologix device," Journal of Vascular Surgery, (2001), vol. 33, No. 2, 154-156.

Christopher K. Zarins, et al. AneuRx stent graft versus open surgical repair of abdominal aortic aneurysms: Multicenter prospective clinical trial, Journal of Vascular Surgery, (1999), vol. 29, No. 2, 292-308.

Ancure P990017 /S030A, Jul. 2, 2002.

Ancure Summary of Safety and 30A Effectiveness Data, Apr. 24, 2002.

Ancure Instruction for Use 30C P990017 /S030C, Apr. 24, 2002.

Ancure Essential Prescribing Information (EPI) and Operator's Instructions for Use, Sep. 28, 1999.

Excluder Approval P020004A, Nov. 6, 2002.

Excluder Summary of Safety and Effectiveness P020004B, Nov. 6, 2002.

Excluder Labeling P020004C, Nov. 6, 2002.

Excluder Brochure P020004D, Nov. 6, 2002.

AneuRx Approval P990020A, Sep. 28, 1999.

AneuRx Summary of Safety and Effectiveness P990020B, Sep. 28, 1999.

AneuRx Instmctions for Use P990020C, Sep. 28, 1999.

Zenith Approval P020018A, May 23, 2003.

Zenith Summary of Safety and Effectiveness P020018B, May 23, 2003.

Zenith Label P020018C, May 23, 2003.

\* cited by examiner

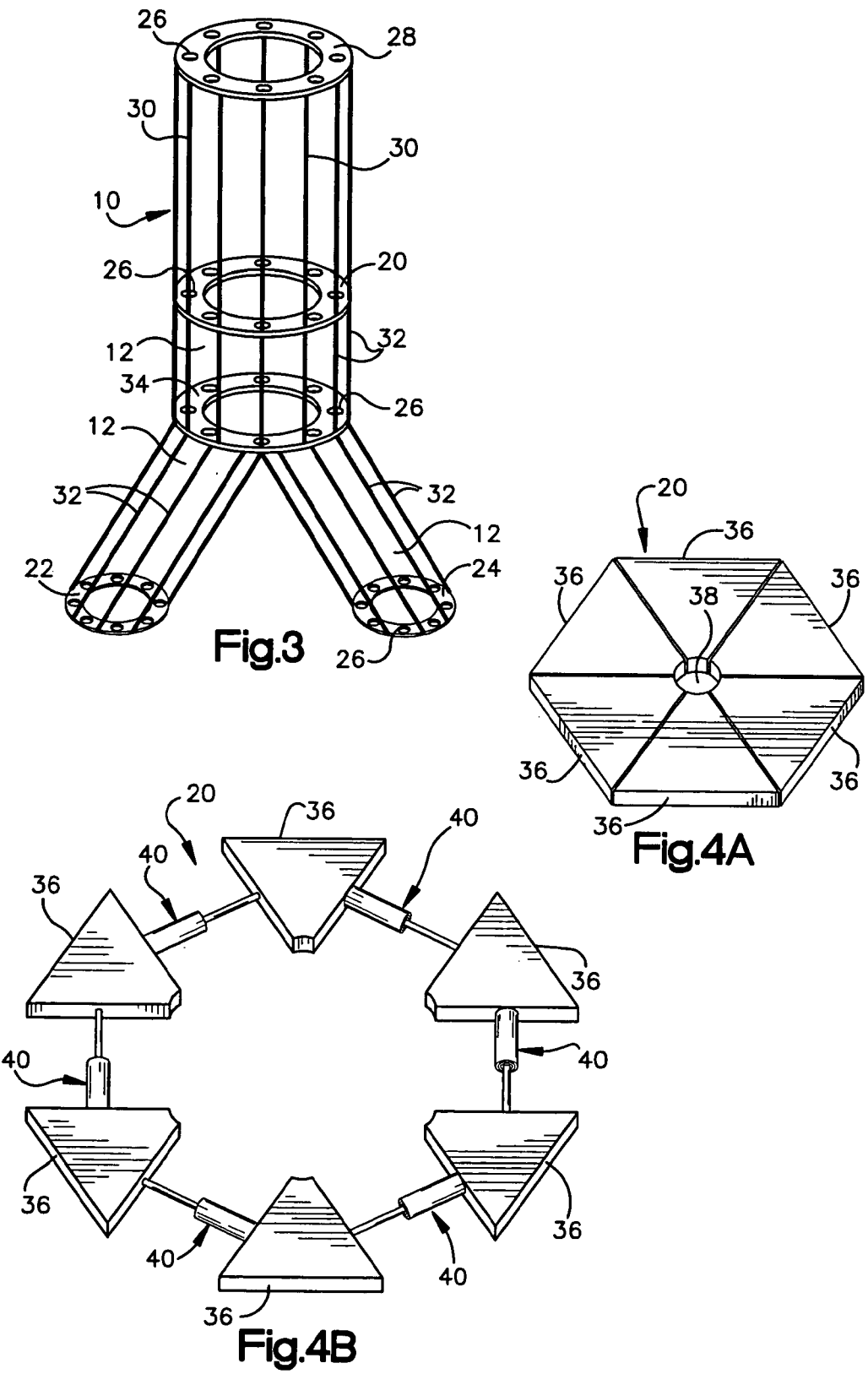

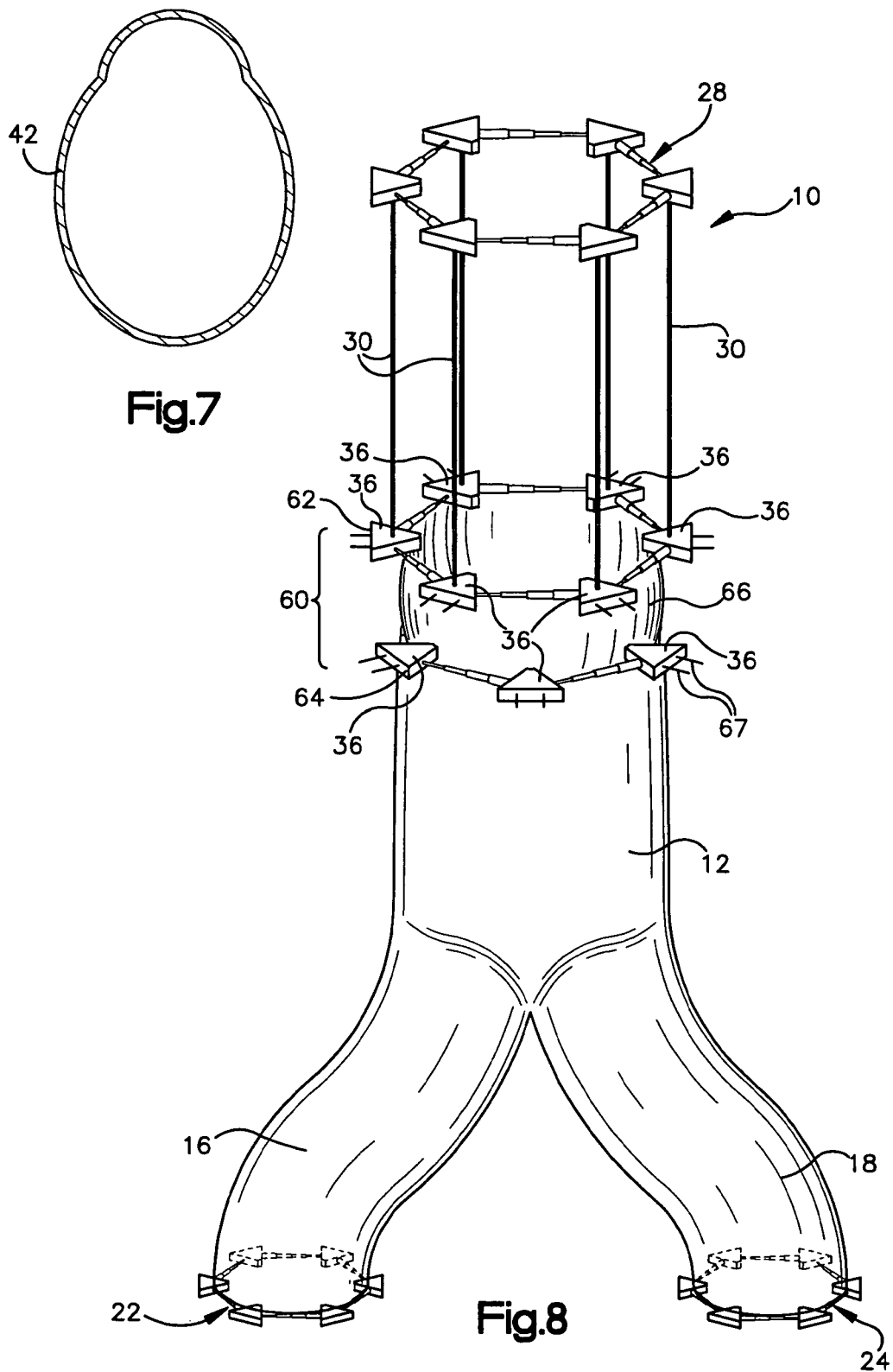

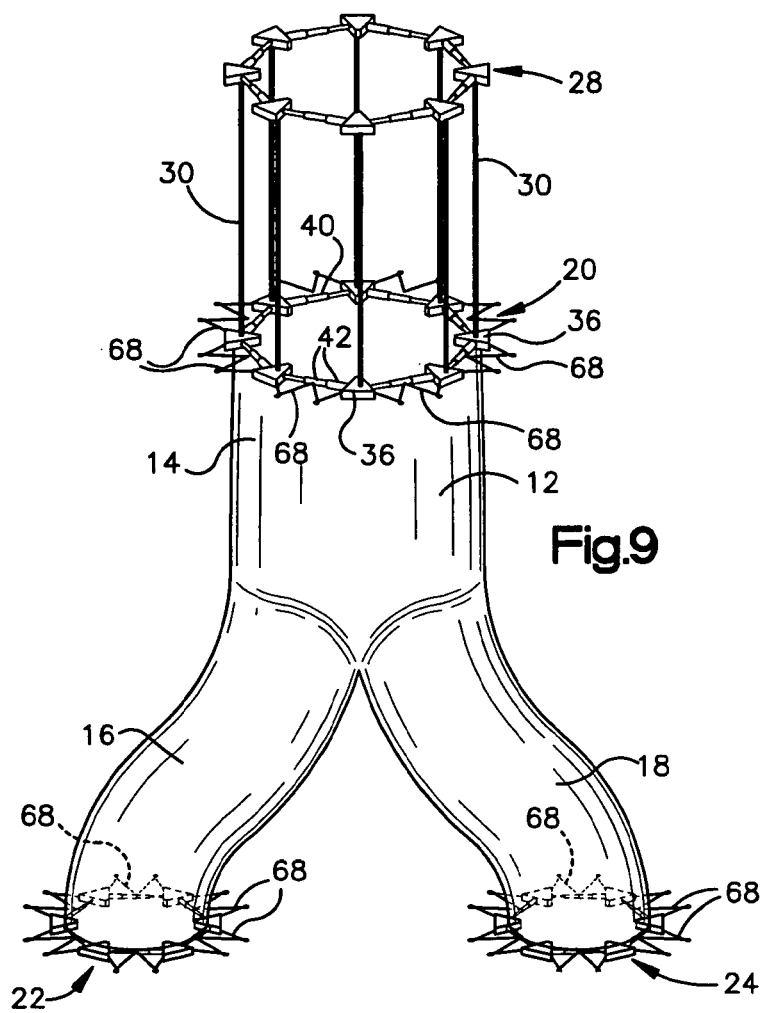
Fig.9
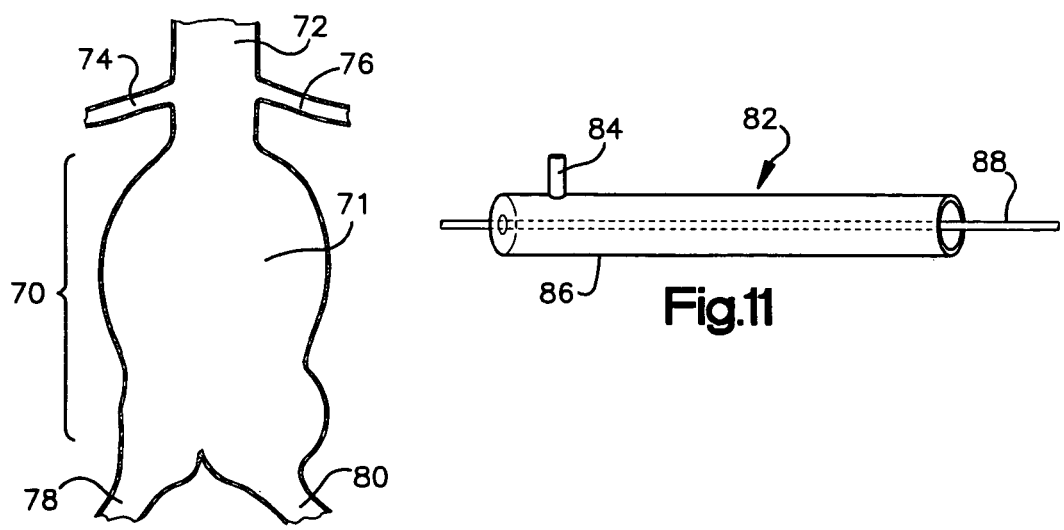
Fig.10
Fig.11

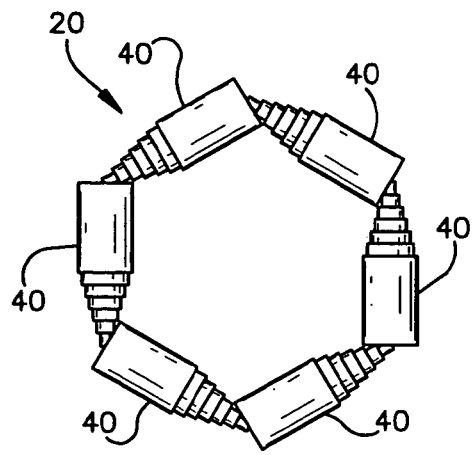 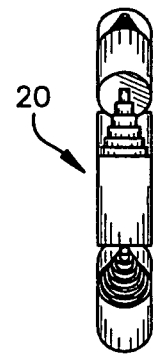
Fig.12A  Fig.12C
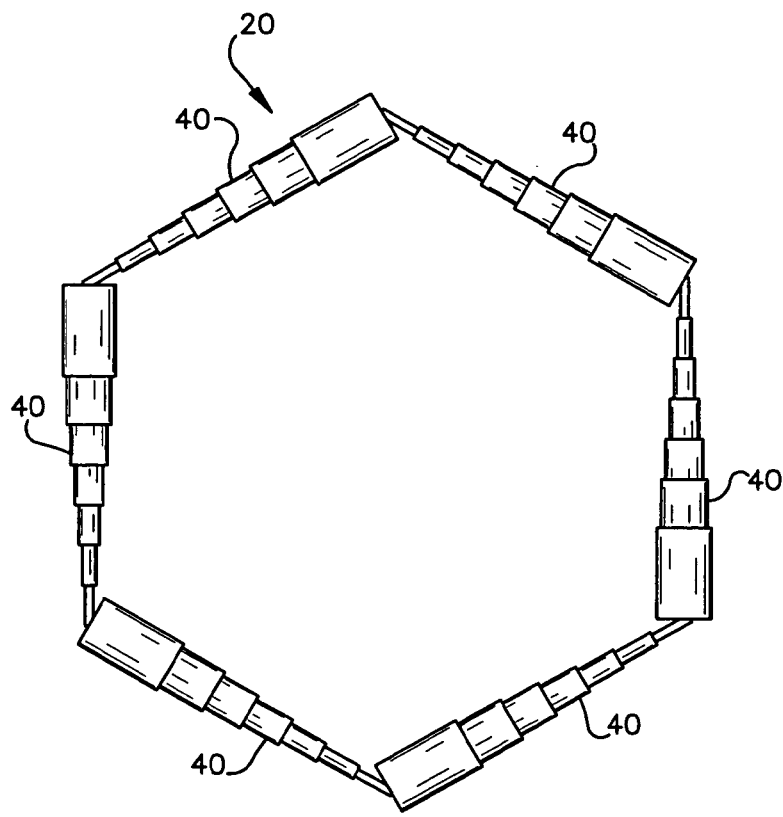 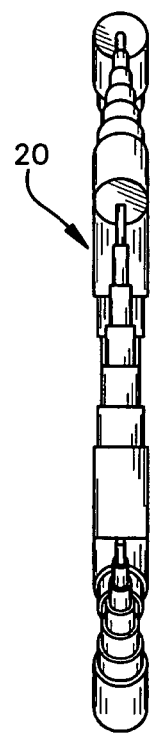
Fig.12B  Fig.12D

PERCUTANEOUS ENDOVASCULAR APPARATUS FOR REPAIR OF ANEURYSMS AND ARTERIAL BLOCKAGES

RELATED APPLICATIONS

This application claims priority to and is a continuation-in-part of U.S. patent application Ser. No. 10/624,864, filed Jul. 22, 2003, now U.S. Pat. No. 7,101,393, issued on Sep. 5, 2006, which in turn claims priority to U.S. Provisional Application No. 60/397,745, filed Jul. 22, 2002. Each of the priority applications is hereby incorporated by reference in its entirety.

FIELD OF THE INVENTION

The present invention relates generally to an endovascular apparatus for the treatment of aneurysms or arterial blockages, and more particularly, to an endovascular apparatus having an expandable attachment device for securing the endovascular apparatus to an interior wall of a lumen.

BACKGROUND OF THE INVENTION

An abdominal aortic aneurysm is an abnormal enlargement or "ballooning out" of the arterial wall of the aorta in a region that passes through the abdominal cavity, usually below the renal arteries and above the common iliac arteries. The aneurysm may also extend into the common iliac arteries. Such aneurysms are typically brought on by the weakening of the arterial wall from vascular disease. Although abdominal aortic aneurysms often do not cause pain, unless treated, an aneurysm may rupture causing a fatal hemorrhage in a patient.

In the past aortic aneurysms were treated almost exclusively by surgical repair. Specifically, the aneurysm would be resected and replaced by an artificial artery known as a prosthetic graft. Because of the substantial risks associated with such an invasive surgery, however, other treatments for aortic aneurysms have been proposed including endovascular grafting.

Endovascular grafting involves the placement of a prosthetic graft within the lumen of the artery such that the graft spans the length of the aneurysm. In this manner the aneurysm can be excluded from the circulatory system rather than resected. Using a catheter as a deployment device, the endovascular graft can be introduced into the vascular system percutaneously. Once the graft has been positioned at the site of the aneurysm it can be attached to the vascular wall both above and below the aneurysm using expandable attachment devices to prevent movement of the graft after deployment.

To introduce an endovascular graft percutaneously, the graft must be collapsible into a small profile for negotiating the vascular system. Upon reaching the site of the aneurysm the graft and its attachment devices can be expanded into a desired shape using an inflating balloon catheter or other actuator. A variety of expandable attachment devices have been proposed for securing an endovascular graft to an interior wall of a vessel most of which use stents with hooks or barbs to penetrate the intima of the vessel. None of the proposed attachment devices, however, have been found to be ideally suited for use with an endovascular graft.

Accordingly an endovascular apparatus having a new expandable attachment device is desired. The new attachment device ideally should be small with a low profile and should expand to many times its initial diameter. It also should exert enough radial force when expanded to fix into the aorta and thereby reduce blood leaks around the apparatus.

SUMMARY OF THE INVENTION

In a first aspect, an expandable attachment device for securing an endovascular apparatus to an interior wall of a lumen is provided. The expandable attachment device may include a plurality of telescoping arms that are joined together to form an expandable ring. This ring may function similarly to stents. The expandable attachment device may be attached to an endovascular apparatus for the treatment of aneurysms or blockages, such as a graft or stent, or to a heart valve and may include barbs, hooks, or other fasteners about its perimeter for attaching to the interior wall of a lumen. Because the attachment device can be collapsed to a size that can be fed through a vessel, the attachment device and an associated endovascular apparatus can be deployed percutaneously in a patient. Once positioned at the site of an aneurysm or arterial blockage, the telescoping attachment device can be expanded to hold the endovascular apparatus in place adjacent the inner lumen wall.

In a second aspect, an endovascular apparatus is provided for treating aneurysms or arterial blockages using a minimally invasive technique. The apparatus includes a tubular sleeve having a cranial end and at least one caudal branch. If the tubular sleeve includes a first caudal branch and a second caudal branch then the tubular sleeve is shaped like an upside down "Y." Accordingly, for the treatment of abdominal aortic aneurysms the cranial end may be positioned in the infrarenal aorta, the first caudal branch may be positioned in one of the common iliac arteries, and the second caudal branch may be positioned in the other common iliac artery. The tubular sleeve may be made from materials conventionally used to make endovascular grafts including synthetic fabrics or films, DACRON™ (synthetic polyester), or expanded polytetrafluoroethylene (ePTFE) so as to define a lumen and so as to be collapsible during percutaneous insertion into a patient's vascular system.

The endovascular apparatus further includes an expandable attachment device attached to the cranial end of the tubular sleeve for securing the apparatus to an interior wall of a vessel above an aneurysm. The expandable attachment device comprises a plurality of telescoping arms that are attached to form an expandable ring. Each telescoping arm is similar to an expandable presentation pointer. Alternatively, each telescoping arm may function like an accordion. Accordingly, during percutaneous insertion of the endovascular apparatus into a patient, the attachment device can be collapsed into a small profile. Once the apparatus is positioned at the site of the aneurysm or blockage, the expandable attachment device can be expanded to hold the endovascular apparatus in place adjacent the inner lumen wall. Fixation components may be positioned around the perimeter of the attachment device and may be partially embedded in the inner wall of the vessel to secure the attachment device.

The plurality of telescoping arms may be made from materials suitable for use in the human body including stainless steel, plastic, or an alloy of nickel and titanium generally known as NITINOL™. NITINOL is commonly used in the manufacture of medical devices that are to be deployed in a compressed state through a catheter because of its unique thermal memory properties. For example, a NITINOL part may be manufactured in a first condition and then cooled and compressed into a second condition. When heated to the body temperature of the patient the NITINOL part will expand to its original first condition.

In another aspect one or more expandable attachment devices may be attached to the one or more caudal branches of the tubular sleeve for securing the one or more caudal branches to the interior of the vessel wall.

BRIEF DESCRIPTION OF THE DRAWINGS

FIG. 3 is a schematic illustration of an endovascular apparatus according to a second aspect;

FIG. 4A is a top view of an expandable attachment device according to a first aspect in a fully collapsed state;

FIG. 4B is a top view of the expandable attachment device of FIG. 4A in a partially expanded state;

FIG. 7 is a cross section of a segment of a telescoping arm according to a first aspect;

FIG. 8 is an endovascular apparatus according to a third aspect;

FIG. 9 is an endovascular apparatus according to a fourth aspect;

FIG. 10 is an illustration of a typical abdominal aortic aneurysm located in the infrarenal aorta;

FIG. 11 is a catheter for percutaneous introduction of an endovascular apparatus into a body lumen;

FIG. 12A is a schematic top view of an expandable attachment device according to a second aspect in a partially expanded state;

FIG. 12B is a schematic top view of the expandable attachment device of FIG. 12A in a fully expanded stated;

FIG. 12C is a schematic side view of the expandable attachment device of FIG. 12A;

FIG. 12D is a schematic side view of the expandable attachment device of FIG. 12B;

DETAILED DESCRIPTION OF THE PREFERRED EMBODIMENT

Figure 1:
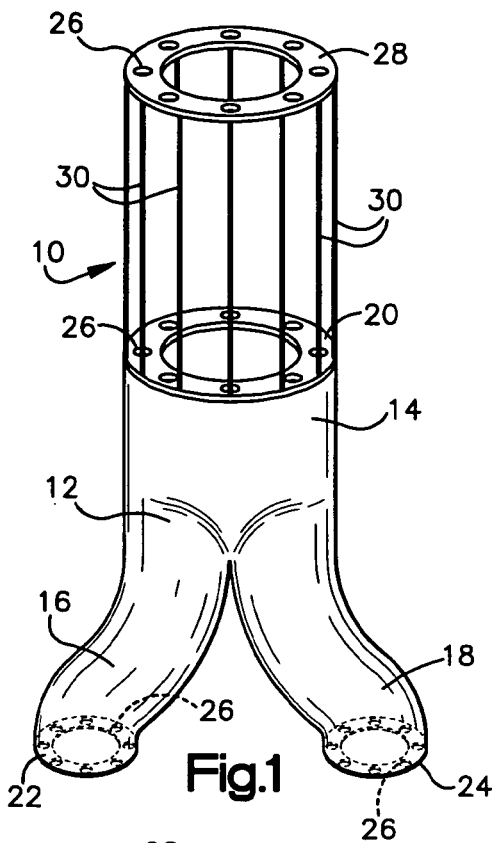
FIG. 1 is a schematic illustration of an endovascular apparatus according to a first aspect.

An endovascular apparatus 10 according to a first aspect is shown in FIG. 1. The endovascular apparatus 10 includes a tubular sleeve 12 having a cranial end 14, a first caudal branch 16, and a second caudal branch 18. In other embodiments, termed "uni-iliac" devices, the tubular sleeve 12 may include only a single caudal branch. The tubular sleeve may be made from DACRON™ (synthetic polyester), ePTFE, peritoneum, fascia, or other common graft material so as to form a flow path for by-passing an aneurysm.

The endovascular apparatus 10 further includes a first expandable attachment device 20 attached to the cranial end 14 of the tubular sleeve 12, a second expandable attachment device 22 attached to the first caudal branch 16 of the tubular sleeve 12, and a third expandable attachment device 24 attached to the second caudal branch 18 of the tubular sleeve 12. The expandable attachment devices 20, 22, 24 may include holes 26 which may be sewn or sutured to the tubular sleeve 12. Alternatively, in lieu of holes 26, the expandable attachment devices can be woven into the sleeve.

In another embodiment, the endovascular apparatus 10 may include a fourth expandable attachment device 28 that is attached to the first expandable attachment device 20 by support columns 30. The fourth expandable attachment device 28 may be positioned above a patient's renal arteries, superior mesenteric artery or celiac artery. The support columns 30, which may be made from NITINOL or stainless steel, may provide columnar support and strength for the endovascular apparatus 10 while permitting blood flow to arteries located between the first expandable attachment device 20 and the fourth expandable attachment device 28.

Figure 14:
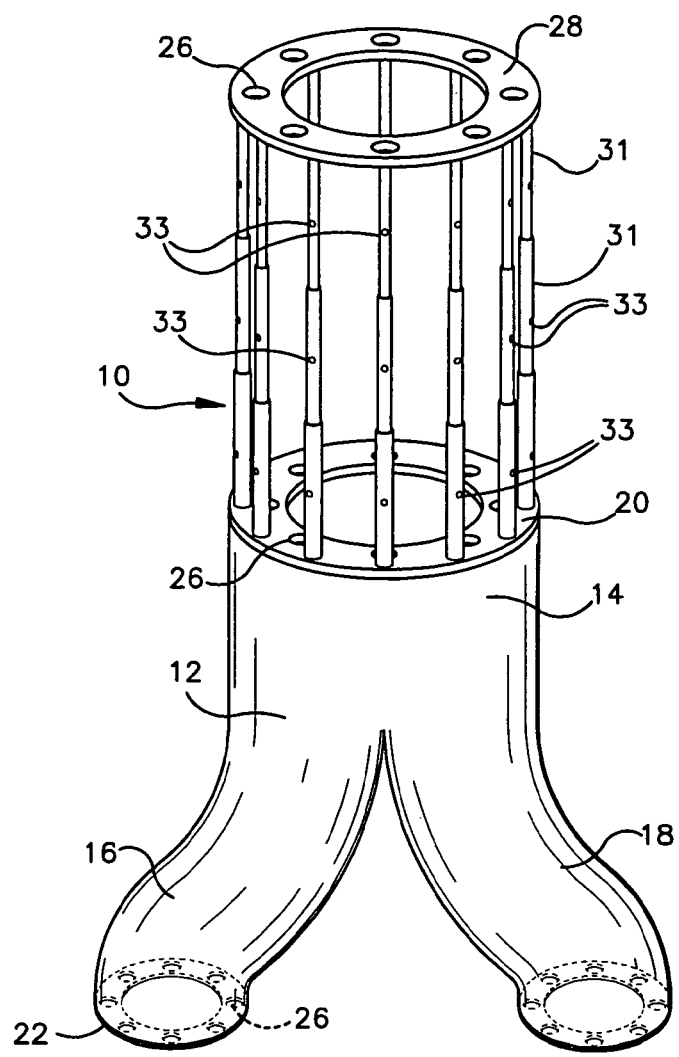
FIG. 14 is a schematic illustration of the endovascular apparatus of FIG. 1 having telescoping support columns.

The support columns 30 may be either wires or tubes. If tubular, the support columns 30 may also be telescoping. For example, in another embodiment depicted in FIG. 14, the support columns 31 may comprise a plurality of incrementally sized segments that are slideably engaged and fit within one another. Thus, in this embodiment the endovascular apparatus 10 may be inserted percutaneously into a vessel with the support columns 31 contracted such that the axial distance between the first expandable attachment device 20 and the fourth expandable attachment device 28 is reduced. During deployment of the endovascular apparatus 10 the support columns 31 may be expanded, thereby permitting the first expandable attachment device 20 to be positioned below the renal arteries while the fourth expandable attachment device is positioned above the renal arteries. In yet another embodiment, shown in FIG. 14, the tubular support columns 30, 31, whether telescoping or not telescoping, may contain an adhesive and include ports or apertures 33 such that the adhesive can escape the support columns 30, 31 upon deployment to assist in securing the endovascular apparatus 10 to the wall of a vessel.

Figure 2A:
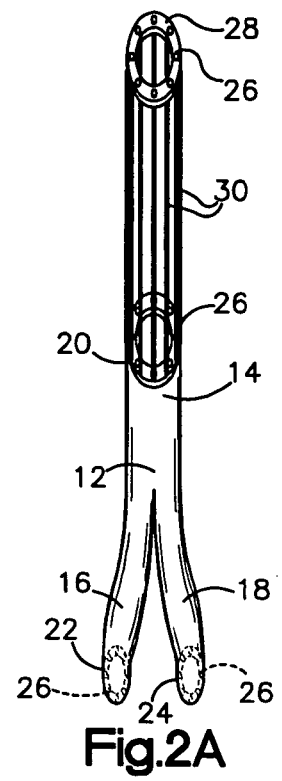
FIGS. 2A-D show the endovascular apparatus of FIG. 1 in various states or expansion.
Figure 2B:
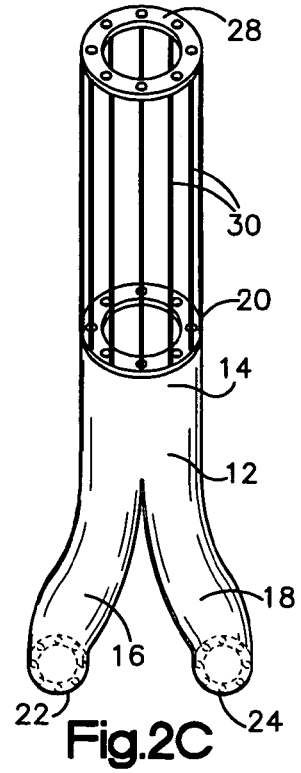
Figure 2C:
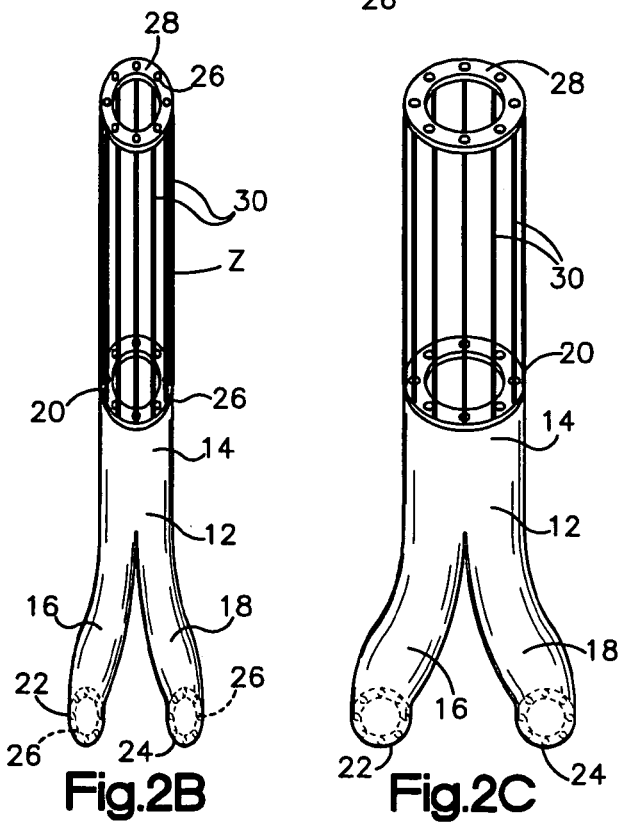
Figure 2D:
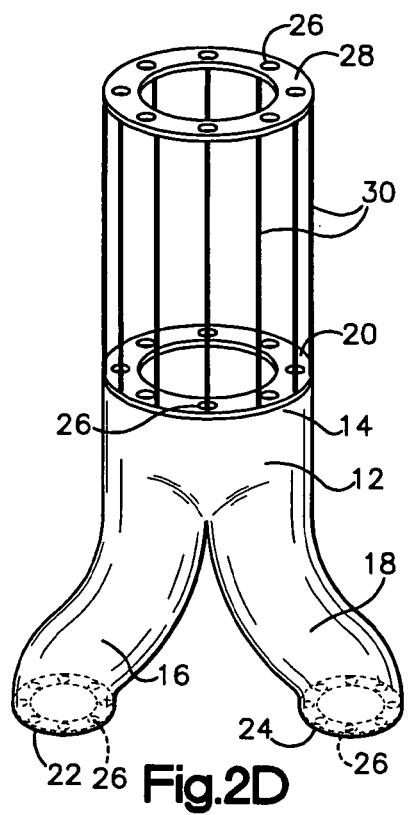

As illustrated in FIGS. 2A-2D, the endovascular apparatus 10 is collapsible for easy insertion and navigation through a patient's vascular system using a catheter. Particularly, as illustrated in FIG. 2A, the attachment devices 20, 22, 24, and 28 may be radially collapsed into a profile that is small enough to fit in a catheter sheath. When the attachment devices 20, 22, 24, 28 are deployed from the sheath at body temperature, the devices may be expanded by a balloon or other actuator to a size and shape in which they are able to retain the sleeve 12 against the wall of a vessel.

The endovascular apparatus 10 according to a second aspect is shown FIG. 3 in which the tubular sleeve 12 is supported by support columns 32. The support columns 32 may attach the first expandable attachment device 20 to a fifth expandable attachment device 34. Likewise, the support columns 32 may attach the second and third expandable attachment devices 22, 24 to the fifth expandable attachment device 34 which may be located at the juncture of the first caudal branch 16 and the second caudal branch 18 of the tubular sleeve 12. In addition the support columns 32 may be sewn or sutured to the exterior of the tubular sleeve 12. This may provide continued columnar support throughout the endovascular apparatus 10 to prevent migration within the vessel. The support columns 32 may be telescoping as described with respect to FIG. 14.

Figure 4C:
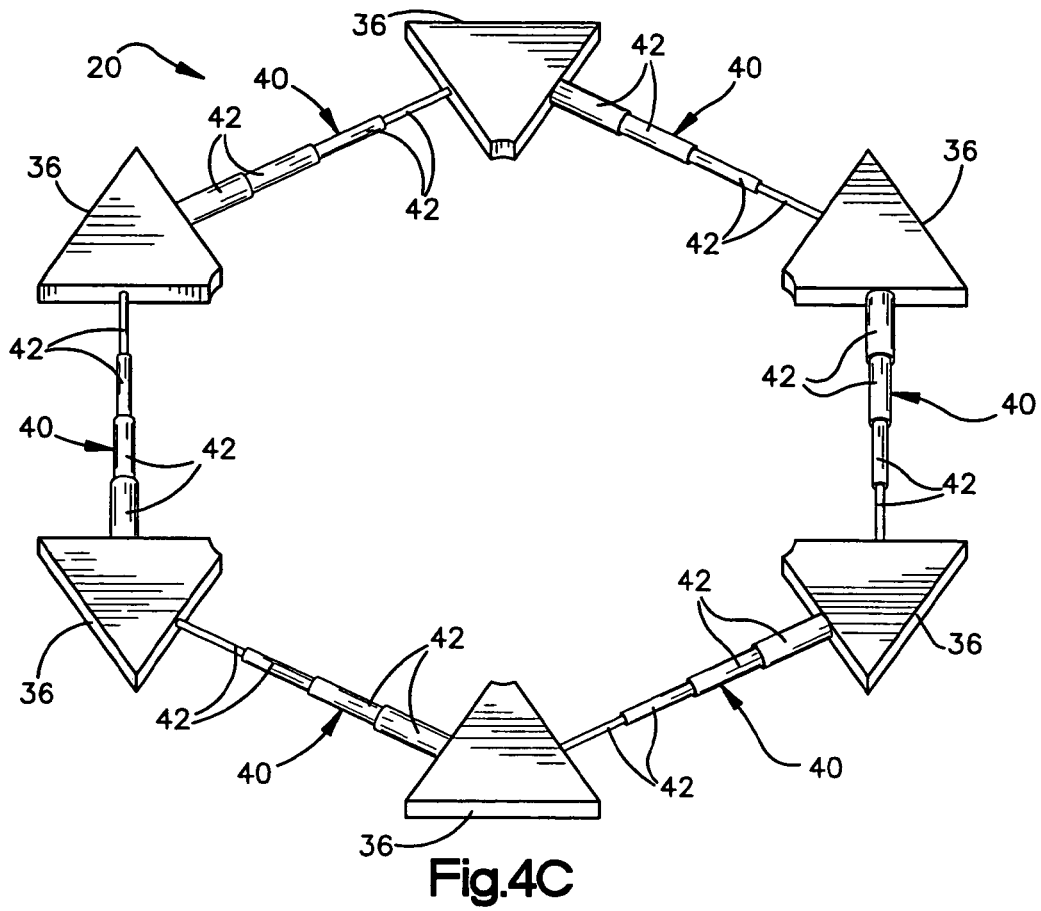
FIG. 4C is a top view of the expandable attachment device of FIG. 4A in a fully expanded stated.

Referring to FIG. 4A, an expandable attachment device 20 according to a first aspect is shown in a fully collapsed state. The attachment device 20 includes a plurality of fixation components 36 positioned about the perimeter of the device 20. A port 38 is located at the center of the attachment device 20. The port 38 is sized so as to receive a balloon or other actuator during deployment. The balloon may be inflated to expand the attachment device 20 after insertion into a vessel. FIG. 4B shows the attachment device 20 in a partially expanded state. FIG. 4C shows the attachment device 20 in a fully expanded state. While in a preferred embodiment, the fixation component can have angular corners, in other embodiments, the fixation component can have curved, rounded, or ovoid edges. Similarly, the entire corner or edge of each fixation component need not be the same shape throughout the length of the edge or corner.

Figure 16:
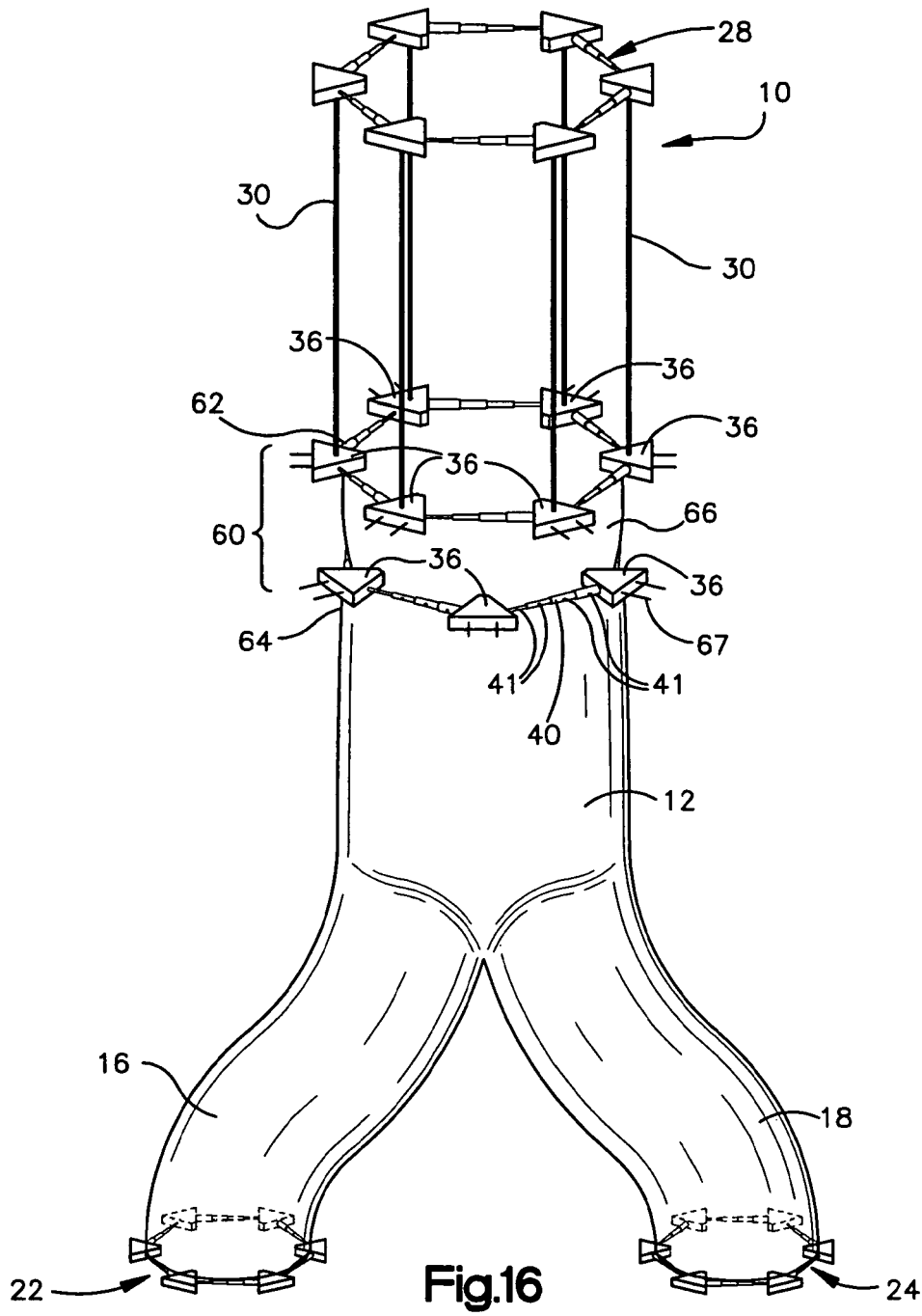
FIG. 16 is a schematic illustration of an expandable attachment device according to another aspect.

Referring to FIG. 4C, a telescoping arm 40 is used to attach each fixation component 36 to an adjacent fixation component 36. The telescoping arm 40 may be pivotably attached to a fixation component 36 at one or both ends of the arm 40. A telescoping arm 40 is made up of a plurality of segments 42. The segments 42 may be in slideable contact with one another and may be incrementally sized so as to fit within one another. For example, each telescoping arm 40 may be constructed from what is referred to generally as "nested tubes." When the telescoping arms 40 are fully extended the attachment device 20 may resemble a polygon having fixation components 36 located at its vertices. The fixation components 36 may include barbs or prongs 67 (shown in FIG. 8) for fixation to a vessel wall. In another embodiment shown in FIG. 16, the telescoping arms 40 may contain an adhesive and include ports or apertures 41 such that the adhesive can escape the telescoping arms upon deployment to assist in securing the endovascular apparatus 10 to the wall of a vessel.

Figure 13A:
FIGS. 13A-G are schematic top views of an expandable attachment device according to a third aspect in various states of expansion.
Figure 13B:
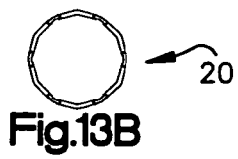
Figure 13C:
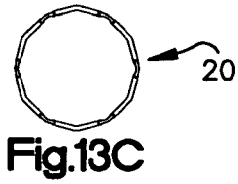
Figure 13D:
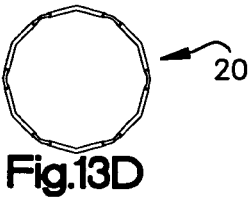
Figure 13E:
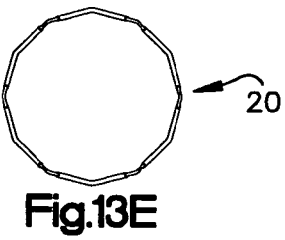
Figure 13F:
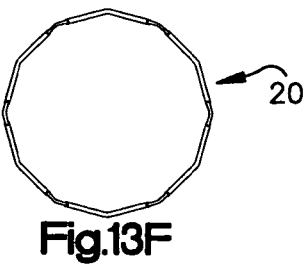
Figure 13G:
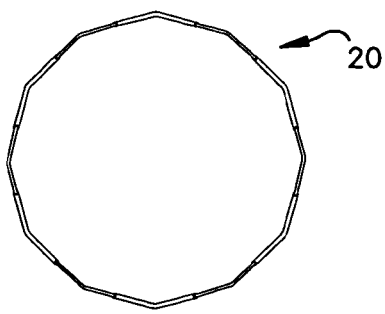
Figure 13H:
FIGS. 13H-N are schematic side views of the expandable attachment device of FIGS. 13A-G.
Figure 13I:
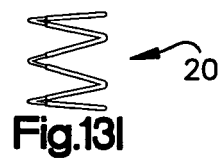
Figure 13J:
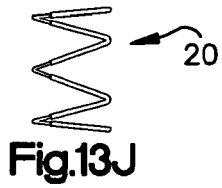
Figure 13K:
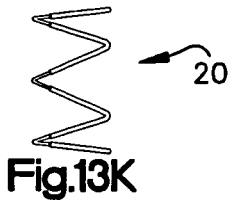
Figure 13L:
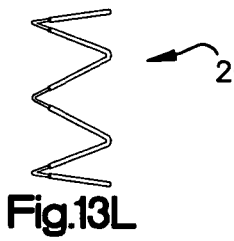
Figure 13M:
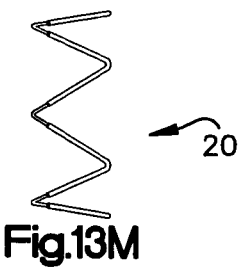
Figure 13N:
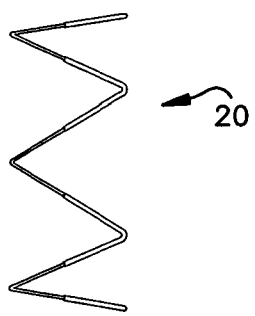
Figure 13O:
FIGS. 13O-T are schematic isometric views of the expandable attachment device of FIGS. 13A-G.
Figure 13P:
Figure 13Q:
Figure 13R:
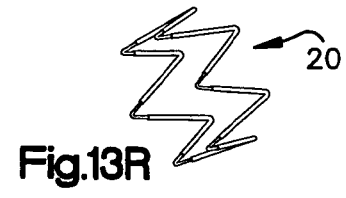
Figure 13S:
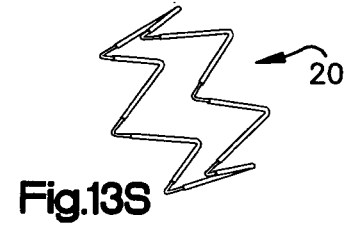
Figure 13T:
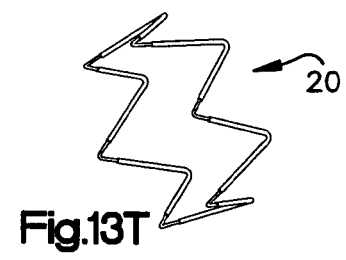

As one of ordinary skill might appreciate, the attachment device may take variety of shapes depending upon the configuration of the telescoping arms 40 and the fixation components 36. For example, referring to FIGS. 12A-D, the telescoping arms 40 may be positioned in a single plane. Alternatively, referring to FIGS. 13A-T, the telescoping arms 40 may be positioned in multiple planes in, for example, what is referred to herein as an "M configuration." One possible advantage of the M configuration is that it may produce superior radial force for holding the attachment device in position. In addition, the M configuration may produce the same ratio of expansion (i.e., the ratio of the final outer diameter of the attachment device in its expanded state to the initial outer diameter of the attachment device in its collapsed state) as the "single plane configuration" using fewer parts.

Figure 13U:
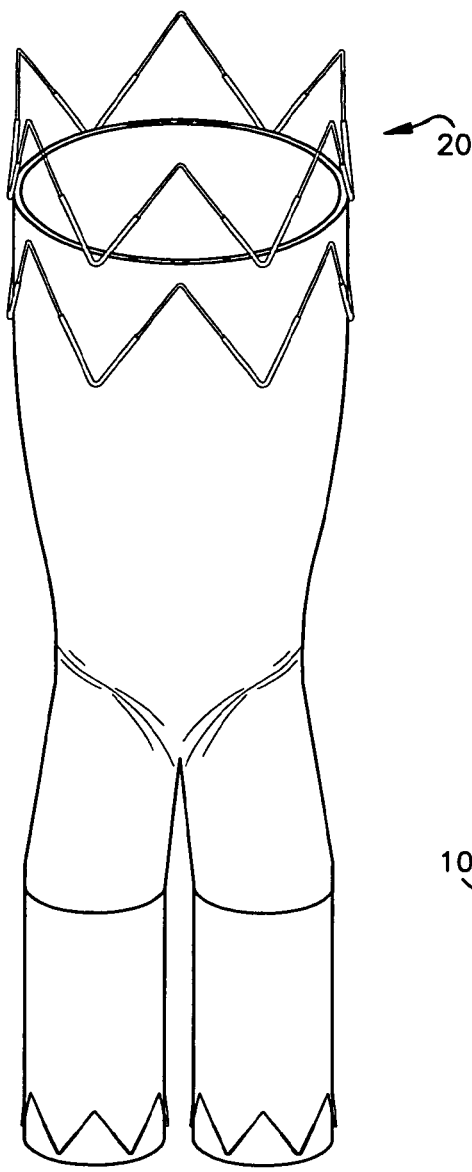
FIG. 13U is a schematic illustration of another embodiment of the invention.

FIG. 13U depicts multiple "M configuration" attachment devices on an endovascular apparatus.

Figure 5:
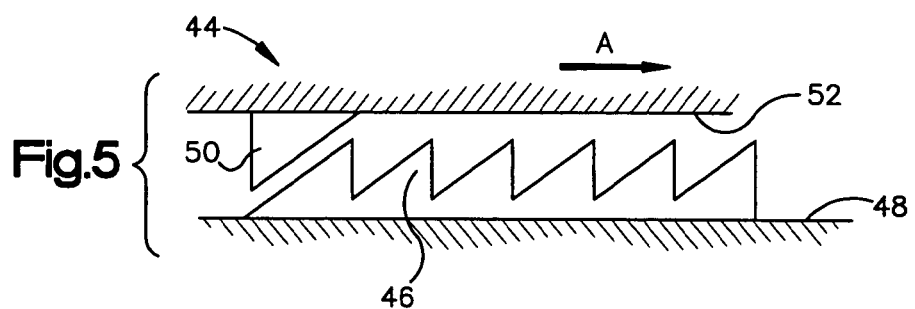
FIG. 5 is a locking mechanism according to a first aspect in a first position.
Figure 6:
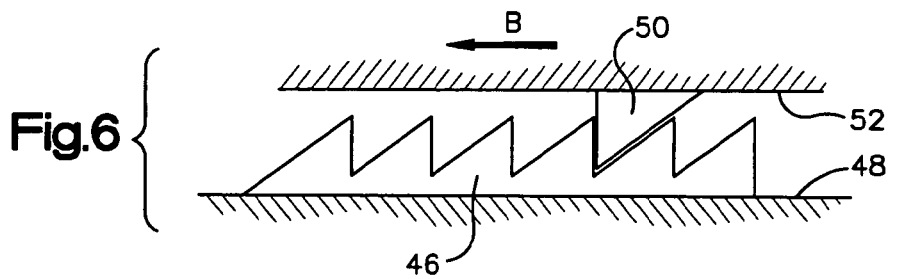
FIG. 6 is the locking mechanism of FIG. 5 in a second position.

To keep the telescoping arms 40 in their final extended state after deployment in a vessel, a one-way latch may be used to lock adjacent segments 42. FIG. 5 shows one possible latch 44, in a first position, for locking the telescoping arms 40. The latch 44 may consist of a one or more grooves 46 associated with a first segment 48 and a tooth 50 associated with a second, adjacent segment 52. As the telescoping arm 40 is expanded, the second segment 52 moves in a first direction A relative to the first segment 48. The tooth 50 and the grooves 46 are aligned so as to engage when the telescoping arm 40 is extended. Once the tooth 50 engages a groove 46, as shown in FIG. 6, the second segment 52 may not move in a second direction B relative to the first segment 48. Accordingly, the telescoping arm 40 is free to extend but may not collapse once extended. Of course other one-way latches may be used to lock the segments 42 of the telescoping arms 40. FIG. 7 illustrates one possible cross-section of a segment 42 of the telescoping arm 40. This "rail" design permits room for sliding and positioning of a one-way latch, like the one shown in FIG. 5, between segments 42 shown in FIG. 4.

FIG. 8 shows the endovascular apparatus 10 according to a third aspect. In the embodiment shown in FIG. 8, the endovascular apparatus 10 includes a double-expandable attachment device 60 in the place of the first expandable attachment device 20. The double-expandable attachment device 60 comprises an upper expandable attachment device 62 and a lower expandable attachment device 64 which are separated by and attached to an o-ring seal 66. The upper attachment device 62 is angularly offset from the lower attachment device 64 so that the fixation components 36 of each are offset. The fixation components 36 may include prongs or barbs 67 to aid in securing the expandable attachment devices 62, 64 to the vessel wall. This design provides for secure attachment to the vessel wall with reduced leakage around the perimeter of the attachment device 60. The lower expandable attachment device 64 may be attached to the tubular sleeve 12. The upper expandable attachment device 62 may be attached to the fourth expandable attachment device 28 by support columns 30.

Figure 15:
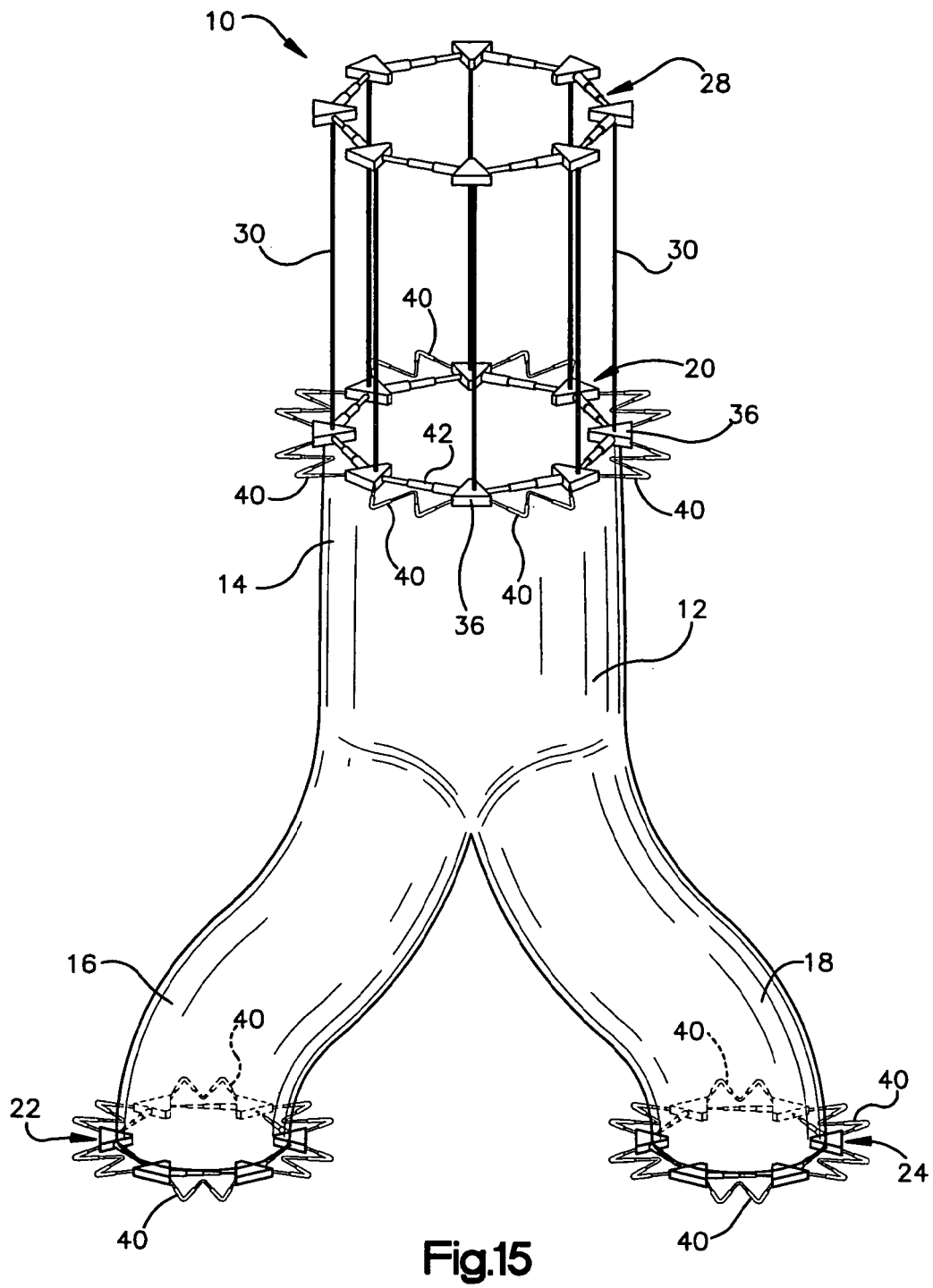
FIG. 15 is a schematic illustration of an endovascular apparatus according to another aspect.

Referring to FIG. 9, the endovascular apparatus 10 according to fourth aspect is shown. In this embodiment a plurality of "M springs" 68 are attached to the cranial end 14 of tubular sleeve 12 as graft expanders in order to hold the tubular sleeve 12 open. In this manner the M springs 68 may reduce leakage around the perimeter of the tubular sleeve 12. M springs 68 may also be used to hold the caudal ends 16, 18 of the tubular sleeve 12 open. In the embodiment shown in FIG. 9, the M springs 68 are not attached to the segments 52 of the telescoping arms 40 and are located on the exterior of the tubular sleeve 12. In another embodiment, the M springs 68 may be located on the interior of the tubular sleeve 12 or attached to the fixation components 36. Of course, in place of the "M springs" 68, springs in the shape of a "V" may be used. Alternatively, in another embodiment depicted in FIG. 15, the M springs 68 may be replaced by telescoping arms 40 in an "M configuration."

FIG. 10 illustrates a typical abdominal aortic aneurysm 70 located in the infrarenal aorta 71. The infrarenal aorta 71 is that portion of the aorta 72 located below the renal arteries 74, 76. As shown in FIG. 10, abdominal aortic aneurysms typically occur below the renal arteries 74, 76 and above the common iliac arteries 78, 80. In some cases, the aneurysm includes the common iliac arteries 78, 80. The endovascular apparatus 10 may be used to treat or repair an abdominal aortic aneurysm 70, like the one shown in FIG. 10, by excluding the weakened aneurysmal aortic wall from pressurized and pulsatile flow. In addition, the endovascular apparatus may be used to treat aneurysms or blockages located in other body lumens such as the thoracic aorta, iliac arteries, subclavian arteries, urinary tract, bile tract, intestinal tract, etc.

Figure 17:
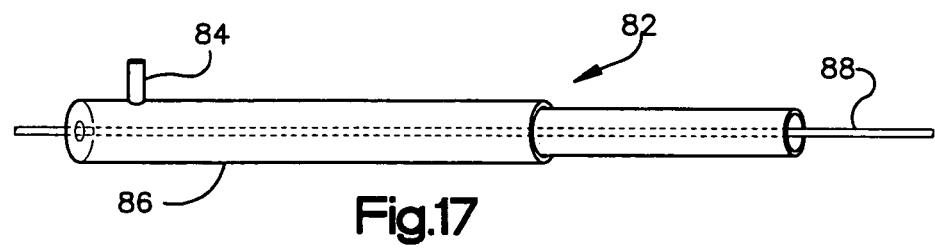
FIG. 17 is a schematic illustration of a telescoping catheter for percutaneous introduction of an endovascular apparatus into a body lumen.

The endovascular apparatus 10 may be deployed at the site of an aneurysm percutaneously using a catheter 82 like the one shown in FIG. 11. The catheter 82 may have an IV port 84, a sheath 86 and an introducer 88 which can be withdrawn within the sheath 86. Using the catheter 82, the device can be introduced percutaneously through either of the femoral arteries. As shown in FIG. 17, using a "nested tube" design similar to the one utilized by the telescoping arms of the attachment device 20, the catheter 82 may also be made to be telescoping.

During deployment the first expandable attachment device 20 may be positioned just below the renal arteries 74, 76 and seated with an expandable balloon or other actuator. The fourth expandable attachment device 28 may be positioned superior to the renal arteries 74, 76, the mesenteric artery, or the celiac artery and seated with an expandable balloon. After the first attachment device 20 is seated, the second expandable attachment device 22 may be positioned in a first iliac artery 78 and seated with an expandable balloon or other actuator. The third expandable attachment device 24 may be positioned such that it rests at a second iliac artery 80. To position and seat the third attachment device 24, access may be obtained percutaneously through the second iliac artery 80.

What is claimed is:

1. An endovascular apparatus comprising:
   a tubular sleeve having a central lumen with a cranial end portion having a perimeter, a first caudal branch, and a second caudal branch; and
   an expandable attachment device connected to the tubular sleeve at the cranial end portion and includes a plurality of fixation components positioned about the perimeter of the device;
   each of the central lumen, first caudal branch and second caudal branch of the tubular sleeve having a plurality of expandable M springs positioned on an outer surface thereof and extending circumferentially thereabout;
   each of said expandable M springs comprising a pair of outer legs connected to a pair of inner legs, the outer legs and the inner legs configured to form an M shape capable of non-uniform movement upon expansion.

2. The endovascular apparatus of claim 1, wherein the tubular sleeve comprises a synthetic polyester.

3. The endovascular apparatus of claim 1, wherein the tubular sleeve comprises an endovascular graft material.

4. The endovascular apparatus of claim 1, wherein the adjacent outer and inner legs are connected to each other by a single bend.

5. The endovascular apparatus of claim 1, wherein the tubular sleeve comprises a synthetic fabric or film.

6. The endovascular apparatus of claim 5, wherein the synthetic fabric or film is expanded polytetrafluoroethylene (ePTFE).

7. An endovascular apparatus comprising:
   a tubular sleeve having a central lumen with a cranial end portion having a perimeter, a first caudal branch, and a second caudal branch; and
   an expandable attachment device connected to the tubular sleeve at the cranial end portion and includes a plurality of fixation components positioned about the perimeter of the device;
   the tubular sleeve having a plurality of expandable M springs positioned on an outer surface thereof and extending circumferentially thereabout;
   each of said expandable M springs comprising a pair of outer legs connected to a pair of inner legs, the outer legs and the inner legs configured to form an M shape capable of non-uniform movement upon expansion.

8. The endovascular apparatus of claim 7, wherein the tubular sleeve comprises a synthetic polyester.

9. The endovascular apparatus of claim 7, wherein the tubular sleeve comprises an endovascular graft material.

10. The endovascular apparatus of claim 7, wherein the adjacent outer and inner legs are connected to each other by a single bend.

11. The endovascular apparatus of claim 7, wherein the tubular sleeve comprises a synthetic fabric or film.

12. The endovascular apparatus of claim 11, wherein the synthetic fabric or film is expanded polytetrafluoroethylene (ePTFE).

* * * * *

UNITED STATES PATENT AND TRADEMARK OFFICE
CERTIFICATE OF CORRECTION

| | |
|---|---|
| PATENT NO. | : 11,890,181 B2 |
| APPLICATION NO. | : 11/484331 |
| DATED | : February 6, 2024 |
| INVENTOR(S) | : Sarac |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 276 days.

Signed and Sealed this
Eighth Day of October, 2024

Katherine Kelly Vidal
*Director of the United States Patent and Trademark Office*